United States Patent [19]

Robinson et al.

[11] 4,396,554

[45] Aug. 2, 1983

[54] HYDROCARBON SOLUBLE DIALKYL MAGNESIUM COMPOSITION

[75] Inventors: Gene C. Robinson; Bonnie G. McKinnie, both of Baton Rouge, La.

[73] Assignee: Ethyl Corporation, Richmond, Va.

[21] Appl. No.: 335,056

[22] Filed: Dec. 28, 1981

[51] Int. Cl.$^3$ ................................................ C07F 3/02
[52] U.S. Cl. ............................ 260/665 R; 252/431 R
[58] Field of Search ................ 260/665 R; 252/431 R

[56] References Cited

U.S. PATENT DOCUMENTS

| | | | |
|---|---|---|---|
| 3,646,231 | 2/1972 | Kamienski et al. | 260/665 R |
| 3,755,478 | 8/1973 | Kamienski et al. | 260/665 R |
| 3,766,280 | 10/1973 | Kamienski et al. | 260/665 R |
| 4,069,267 | 1/1978 | Kamienski et al. | 260/665 R |
| 4,127,507 | 11/1978 | Fannin et al. | 260/665 R X |
| 4,207,207 | 6/1980 | Sanchez et al. | 260/665 X |
| 4,213,880 | 7/1980 | Knight et al. | 252/431 R |
| 4,222,969 | 9/1980 | Fannin et al. | 260/665 R |
| 4,231,896 | 11/1980 | Malpass | 252/431 R |
| 4,299,781 | 11/1981 | Fannin et al. | 260/665 R |

*Primary Examiner*—Helen M. S. Sneed
*Attorney, Agent, or Firm*—Donald L. Johnson; John F. Sieberth; Paul H. Leonard

[57] ABSTRACT

A composition of matter comprising di-isoamylmagnesium and diethylmagnesium, with an isoamyl: ethyl alkyl group ratio of about 1.4 to about 4:1, which is soluble in aliphatic, cycloaliphatic, and aromatic hydrocarbon solvents is disclosed, as is a process for making such mixed dialkylmagnesium wherein magnesium metal is reacted with an ethyl halide and an isoamyl halide in the presence of the hydrocarbon solvent and in a substantially moisture-free and ether-free atmosphere, followed by separation of undissolved solids from the resulting solution.

30 Claims, No Drawings

HYDROCARBON SOLUBLE DIALKYL MAGNESIUM COMPOSITION

BACKGROUND OF THE INVENTION

Diorganomagnesium compounds are well known for their usefulness in a wide variety of chemical reactions. As reagents, these compounds can be used for the alkylation of ketones and the alkylation of metal halides or oxides to the corresponding metal alkyls. As catalysts, diorganomagnesium compounds are useful in the dimerization and polymerization of olefins, see Britain Pat. No. 1,251,177, the polymerization of epoxides, see U.S. Pat. No. 3,444,102, and the preparation of telomers, see U.S. Pat. No. 3,742,077. While they perform many of the same types of functions performed by Grignard reagents, diorganomagnesium compounds, owing to differences in electronic and steric factors, are more reactive than Grignard reagents toward certain types of compounds. In general, see also U.S. Pat. Nos. 3,646,231 and 3,822,219.

The utility of diorganomagnesium compounds is lessened by the fact that many are either solids or highly viscous liquids. This problem is generally overcome either by dissolving the compound in an inert hydrocarbon solvent or by solvating the compound. All are unstable upon exposure to moisture and air and require handling under an inert atmosphere. Some diorganomagnesium compounds, with straight chain lower alkyl groups of up to four carbon atoms, are insoluble by themselves in hydrocarbon solvents and thus require solubilizing agents which will form a soluble complex. Examples of such solubilizing agents are alkyllithium compounds, see U.S. Pat. No. 3,742,077, dialkyl zinc compounds, see U.S. Pat. No. 3,444,102, alkali metal hydrides, see U.S. Pat. No. 3,655,790, and organoaluminum compounds, see U.S. Pat. Nos. 3,737,393 and 3,028,319, and combination of certain dialkylmagnesium compounds in hydrocarbon solvents. See U.S. Pat. Nos. 4,069,267 ($C_1$ to $C_4$ di-n-alkylmagnesium and $C_6$ to $C_{18}$ dialkylmagnesium), 4,127,507 (di-n-butyl magnesium and di-ethyl magnesium), 4,207,207 (di-methyl-magnesium and di-n-propyl magnesium) and 4,222,969 (dimethylmagnesium and di-n-butyl magnesium).

Solvation involves the use of an ether or other organic Lewis base molecule to associate directly with the magnesium atom, thus yielding a hydrocarbon soluble complex. The solvated form is undesirable however, since solvation seriously inhibits the effectiveness of the compound, for some uses, particularly when the compound is used as a Ziegler-type polyethylene catalyst. The use of ether is particularly undesirable because it is flammable and its vapors are explosive. Also, it introduces soluble RMgX according to the Schlenk equilibrium $$R_2Mg + MgX_2 \rightleftharpoons 2RMgX$$

where R is alkyl and X is halogen.

Solubilization also serves to reduce the viscosity of reaction mixtures whose high viscosity would otherwise inhibit the stirring of the reaction mixture and cause difficulty in handling and transferring. This problem is only partially solved by the use of chloroaryl solvents to form low viscosity suspensions of the insoluble compounds, as described in U.S. Pat. No. 3,264,360.

In addition, the insolubility of the lower alkyl magnesium compounds makes preparation of them in a form free of undesirable co-product magnesium halides difficult. In particular the direct reaction of magnesium metal with an organic halide is disclosed in Glaze and Selman, *Journal of Organometallic Chemistry*, Vol. 5. p. 477 (1967), and W. N. Smith, *Journal of Organometallic Chemistry*, Vol. 64, p. 25 (1974). These articles deal with the preparation of diorganomagnesium compounds with straight chain alkyl groups of 5 carbon atoms and higher. Such compounds are soluble in hydrocarbon solvents and thus readily separable from the concurrently produced magnesium halide and unreacted magnesium. When lower straight chain alkyls are used in this process, the desired diorganomagnesium compound is formed but is insoluble and exists as a slurry in the solvent together with the magnesium halide and unreacted magnesium metal. Thus a solubilizing agent is required when this process is used to make lower alkyl diorganomagnesium compounds. The latter are particularly desirable as reagents and catalysts owing to their relatively high magnesium content on a weight basis.

Other methods of preparation include the mercury-magnesium exchange method, as disclosed in Cowan and Mosher, *Journal of Organic Chemistry*, Vol. 27, p. 1 (1962), and the dioxanate-precipitation method, as disclosed in Schlenk, *Berichte der Deutschen Chemischen Gesellschaft*, Vol. 64, p. 734 (1931). The mercury method, $$R_2Hg + Mg \rightarrow R_2Mg + Hg$$

where R is alkyl, is limited by the high cost of dialkylmercury compounds, and the health hazards involved in their use. The reaction itself is hazardous since it proceeds rapidly and exothermically after an inhibition period.

The dioxanate-precipitation method, $$2RMgX + C_4H_8O_2 \xrightarrow{ether} R_2Mg + C_4H_8O_2 \cdot MgX_2$$

where R is alkyl and X is halogen, involves removal of magnesium halide from ether solutions of Grignard reagents by precipitation of a complex which the dioxane forms with the halide. This is a tedious process and results in an etherated dialkylmagnesium complex from which the ether must be removed prior to use as a catalyst component in Ziegler type polymerizations.

Dialkylmagnesiums ca also be prepared from alkyllithiums, see U.S. Pat. No. 3,646,231 by precipitation of lithium halide, $$MgX_2 + 2Li \rightarrow R_2Mg + LiX$$

where R is alkyl and X is halogen. This process is unsuitable for straight-chain lower alkyl diorganomagnesiums which are insoluble in hydrocarbon solvents, since separation from co-product lithium chloride will be impossible. The use of basic solvents renders separation possible but requires subsequent desolvation. U.S. Pat. Nos. 4,127,507; 4,207,207 and 4,222,969, each state that branched chain diorganomagnesium compounds cannot be prepared by the Glaze and Selman method, i.e. the direct reaction of magnesium metal with an organic halide. U.S. Pat. No. 4,069,267 further confirms this wherein it is stated that when pure, dry metallic magnesium is treated with an alkyl halide, in a liquid hydrocarbon solvent such as heptane, cyclohexane, or toluene, it is found that only certain alkyl halides, those of the normal or unbranched variety, e.g., n-butyl chloride react to produce the desired dialkylmagnesiums. Thus, resort to the lithium halide precipitation method is required.

The general insolubility of straight chain lower alkyl magnesium compounds is thought to be due to intermolecular association resulting in the formation of a polymer-type macrostructure wherein each magnesium atom is tetrahedrally surrounded by four short alkyl groups. Known methods of solubilizing these compounds presumably operate to break some of the intermolecular bonds and thereby break down the macrostructure into shorter, more soluble units. Solvation or complexing as described above are thought to bring about this effect.

Alkylmagnesium compounds containing either branched chain alkyl groups or straight chain alkyl groups of five carbon atoms or more, known to be effective as solubilizing agents, may operate by breaking the intermolecular bonds. Probably, the effect occurs by way of alkyl interchange and re-association, whereby the solubilizing alkyl groups exchange positions with some of the straight chain lower alkyls. Solids formation is thus sterically hindered, either because the substituted groups are unwieldy in solids packing, or because the groups have some inherent solubility of their own.

W. Novis Smith, Jr. in the *Journal of Organometallic Chemistry* 64 (1974) pp. 25–40, page 29, states that many attempts were made to obtain sec-dialkyl magnesium compounds in hydrocarbon solvents using the direct reaction of sec-alkyl halide and magnesium, but only very low concentrations were ever obtained and that these were with sec-alkyl iodide in benzene. A small amount of precipitate always formed.

It has been discovered that although branched chain organo magnesium compounds cannot be made from magnesium metal and branched alkyl halides in a hydrocarbon solvent when the halide is 2-halobutane or isobutyl halide, they can be made from 3-methyl-1-halobutane (isoamylhalide), or other remotely branched chain alkyl halides.

It is therefore an object of the present invention to provide hydrocarbon-soluble diorganomagnesium compositions of high magnesium content.

A further object of the present invention is to provide a process by which hydrocarbon soluble diorganomagnesium compositions of high magnesium content can be prepared by the direct reaction of alkyl halides with magnesium.

A still further object of the present invention is to provide a means for solubilizing straight chain lower alkyl diorganomagnesium compounds in hydrocarbon solvents.

Another object of the present invention is to provide a composition of matter comprising di-isoamylmagnesium, diethylmagnesium, and a hydrocarbon solvent.

Yet another object of the present invention is to provide a process for the manufacture of unsolvated branched-chain, lower alkyl diorganomagnesium compounds, namely diisoamylmagnesium.

BRIEF DESCRIPTION OF THE INVENTION

The present invention relates to the discovery that a composition of matter comprising a di-remotely branched chain alkyl magnesium having at least five carbon atoms in the alkyl group and with branching occuring at least three carbon atoms from the magnesium group (e.g. di-isoamylmagnesium) and diethylmagnesium can be made from the reaction of a similarly remotely branched chain alkyl halide (e.g. isoamyl chloride) and ethyl chloride with magnesium powder and is soluble in hydrocarbon solvents. While the latter is not soluble alone, the former has the effect of rendering the other soluble. The composition of this invention optionally contains other components such as solvents, viscosity reducers, cocatalysts, etc., to the exclusion, however, of dialkylmagnesium compounds containing alkyl groups other than isoamyl or ethyl. Related to this discovery is the further discovery that a hydrocarbon-soluble mixture of these two compounds can be prepared by direct reaction between metallic magnesium and each of the two corresponding alkyl halides added in consecutive manner to the same vessel. Such discovery is in contrast to the known behavior of diethylmagnesium, in that when such compound is similarly prepared alone, it is insoluble and thus inseparable from both the concurrently formed magnesium halide and any unreacted magnesium metal remaining in the vessel.

DETAILED DESCRIPTION OF THE INVENTION

In the preferred embodiment of the present invention, di-isoamylmagnesium and diethylmagnesium are combined to provide a composition which is soluble in hydrocarbon solvents.

In lieu of di-isoamyl magnesium, any di-remotely branched chain alkyl magnesium as defined hereinbefore may be used. For example, di-isohexylmagnesium, di-3-methylhexyl magnesium, di-3-ethylhexyl magnesium, di-3-methylheptyl magnesium, di-3-ethylheptyl magnesium, di-4-methylheptyl magnesium, di-4-ethylheptyl magnesium, di-3-methyloctyl magnesium, di-4-methyloctylmagnesium, di-3-ethyloctyl magnesium, di-4-ethyloctyl magnesium and the like.

Similarly, in lieu of isoamyl halide or isoamyl chloride, other remotely branched chain alkyl halides or chlorides may be used. For Example, iso-hexylhalide, isohexyl chloride, 3-methylhexyl halide, 3-methylhexyl chloride, 3-ethylhexyl halide, 3-ethylhexyl chloride, 3-methyl heptyl halide, 3-ethylhexyl chloride, 4-methyl heptyl halide, 4-methylheptyl chloride, 3-methyloctyl halide, 3-methyloctyl halide, 3-methyloctyl chloride, 4-ethyloctyl halide, 4-ethyloctyl chloride and the like.

The term "hydrocarbon solvent" is used herein to designate aliphatic, cycloaliphatic, and aromatic hydrocarbons. Illustrative of aliphatic solvents are n-pentane, isopentane, n-hexane, n-heptane, n-octane, isooctane, pentamethylheptane, and gasoline and other petroleum fractions. Illustrative of cycloaliphatic solvents are cyclohexane, methylcyclohexane, methylcyclopentane, cycloheptane, and cyclooctane. Illustrative of aromatic solvents are benzene, toluene, xylenes, ethylbenzene, tetralin, and α-methylnaphthalene. Preferred solvents are those containing 5 to 20 carbon atoms, inclusive. More preferred are those containing 6 to 15 carbon atoms, inclusive. Particularly preferred solvents are those which have boiling points between about 80° C. and about 150° C.

The concentration of dialkylmagnesium in the solvent is not critical and the compounds are soluble over a wide range of concentration. The solution viscosity increased with concentration, however. For greater ease of handling, therefore, the dialkylmagnesium concentration in terms of magnesium is normally from about 0.2 to about 12.0 weight percent, and preferably from about 1.0 to about 5.0 weight percent.

The solution can be prepared by physically combining the two solid dialkylmagnesium compounds with the hydrocarbon solvent. A clear solution results which is readily separable from any insolubles retained with the compounds.

Thus, di-ethylmagnesium, as a solid or slurry, existing in admixture with magnesium halides other insoluble by-products of the manufacturing process, or unreacted starting materials, can be contacted with a hydrocarbon solvent in the presence of di-isoamylmagnesium, or vice versa, to produce a solution containing the two as solutes, substantially free of the others. Solubilization can be hastened by heating the solution to a temperature of about 50° C. or higher. The rate of solubilization increases as the temperature is raised. Once the compounds are dissolved, they will remain in solution upon any subsequent lowering of temperature.

If desired, separation of the solution from the remaining undissolved solids can be enhanced by the use of any of the variety of viscosity reducing agents known in the art. Examples of such viscosity reducing agents are organoaluminum compounds such as trialkylaluminums, dialkylaluminum halides, alkylaluminum dihalides, dialkylaluminum hydrides and aluminum alkoxides.

Some examples of these organoaluminum compounds or viscosity reducing agents are triethylaluminum, tri-n-propylaluminum, diethylaluminum chloride, ethylaluminum dichloride, isoprenyl aluminum, diethylaluminum iodide, diisobutyl aluminum hydride, and aluminum isopropoxide.

Alternatively, diethylmagnesium and di-isoamylmagnesium can be prepared directly in the solvent in a common vessel by either simultaneous or subsequent reactions. Any reaction is suitable in which neither the by-products nor the unreacted magnesium powder are soluble in the final mixture. The insolubles can be easily separated by settling or by filtration. One such technique involves the direct reaction between metallic magnesium and isoamyl and ethyl halides. The concurrently produced magnesium halide forms a precipitate which is readily removed from the solution together with any unreacted magnesium still present. Another technique involves the use of a Grignard reagent, preferably ethyl magnesium chloride, to supply the ethyl group. The Grignard reagent is preferably freed of all ether used in its preparation prior to its use in the present reaction. The desired solution of isoamyl and ethyl magnesium compounds is then obtained by reaction of the desolvated ethyl Grignard reagent with the reaction product of an isoamyl halide with magnesium metal.

Following any of the above procedures, the solids can be removed from the reaction mixture by any conventional technique, for example, centrifuging, decanting, or filtration. The resulting solution of di-isoamyl magnesium and diethylmagnesium can then be diluted or concentrated to give the concentration desired for purposes of reactivity, viscosity, or economic considerations.

The mutual solubilizing effect is achieved at ethyl-/isoamyl mole ratios of from about 0.2:1 to about 5:1. The preferred range of mole ratios is from about 0.5:1 to about 4:1, with the most preferred range being from about 1:1 to about 2:1.

When magnesium is reacted directly with an alkyl halide, commercial grade magnesium turnings or shavings can be used. It is preferable, however, to use a form of magnesium with a higher surface area than either of the above. This can be accomplished by milling, but it is most preferable to use the metal in a finely divided state, for instance, as a powder with a particle size equal to or less than about 300 microns.

When the magnesium/ethyl halide reaction and the magnesium/isoamyl halide reaction are done in a common vessel, either halide may be added first or the two halides may be co-fed. A magnesium activating agent is normally required to initiate the ethyl halide reaction. The term "magnesium activating agent" is used herein to denote heat or any substance which, when contacted with magnesium, will cause the magnesium to react with the halide at a substantially faster rate. Many activating agents are known in the art. Typical examples are aluminum trichloride, aluminum trichloride-ether complexes; N,N-dimethylaniline, molecular iodine, alkyl halides of at least 3 carbon atoms, and Grignard reagents. A small quantity of isoamyl ethylmagnesium itself can serve as an activating agent. This last is the preferred method.

Once the magnesium is activated, the magnesium/alkyl halide reaction can proceed over a wide temperature range. Generally, it will be most convenient to operate between about 20° C. and about 200° C., preferably between about 50° C. and about 175° C., and most preferably between about 80° C. and about 150° C.

The temperature ranges quoted above are not critical to either reaction. The minimum temperature is dictated largely by process economics, while the maximum temperature is limited mainly by magnesium alkyl decomposition and consideration of energy conservation.

The term "halide" as used herein denotes chloride, bromide, or iodide, or combinations thereof. Chlorides are generally preferred as they are cheaper and provide greater yields.

The reactant mole ratio can be varied over a wide range. No particular range is critical to the performance of either of the two reactions. Normally, however, the starting materials will be such that the mole ratio of magnesium to total halides is from about 1.0 to about 2.0, preferably from about 1.1 to about 1.3. The excess magnesium inherent in mole ratios greater than 1.0 is effective in minimizing Wurtz coupling reactions.

The hydrocarbon solvent may be added before or during the reaction. It will be most convenient to add the solvent prior to the alkyl halide reaction, so that further reaction is less inhibited by high viscosity.

Magnesium alkyls are pyrophoric substances, capable of spontaneous ignition upon contact with air. To prevent such ignition, and also to prevent oxidation of the dialkyl magnesium product, the reactions must be carried out in the absence of more than trace amounts of oxygen. Thus, the reactions are normally carried out in an atmosphere of inert gas such as nitrogen or argon. The reactions must also be conducted in the substantial absence of water, due to the susceptibility of the system components to decomposition in the presence of water.

The pressure under which the reactions are conducted is not critical and pressures ranging from atmospheric to elevated pressures of several atmospheres can be employed. The ethyl halide reaction will be most conveniently run at least in slight excess of atmospheric in order to keep the ethyl halide in solution. The preferred pressure range is about 8 psig ($1.6 \times 10$ pascals) to about 100 psig ($8.0 \times 10^5$ pascals). Lower pressures can be used with the isoamyl halide reaction.

GENERAL PROCEDURE

The present invention is further illustrated by the following examples.

Unless stated otherwise, all reactions were carried out in a 4-neck Morton flask equipped with an ice-water cooled Friedrich's condenser, mechanical stirrer, addition funnel, and thermometer. The transfer of reagents or products was carried out either in a dry nitrogen box or under a nitrogen blanket. All glassware was dried in an oven at 100° C. followed by cooling under nitrogen. All alkyl chlorides, Isopar E (Exxon), and heptane (Phillips Petroleum Co.) were dried over 4 Å molecular sieves. Isopar E is an isoparaffinic solvent in the $C_8$ to $C_9$ region boiling from about 115° C. to about 142° C.

Ethyl chloride was transferred from a weighed container to the addition funnel by means of a Teflon tube which extended beneath the surface of the alkyl chloride-solvent mixture.

EXAMPLE 1

This example illustrates the preparation of isoamylethylmagnesium in a hydrocarbon solvent. The procedure features the reaction of ethyl chloride and isoamyl chloride with metallic magnesium activated by a small amount of dialkylmagnesium and with a small amount of an aluminum compound in the solvent for viscosity reduction.

Following the general procedure outlined hereinabove, the reactor was charged with 36.1 grams (1.48 g-atom) of magnesium powder, 400 ml of heptane, 20 ml of ethyl butylhexylmagnesium (2.8 weight percent Mg) and 3.3 grams of aluminum isopropoxide. A mixture of 43.5 grams (0.675 moles) of ethyl chloride and 82.7 ml (0.675 moles) of isoamyl chloride in 100 ml of heptane was added at heptane reflux over a period of 4½ hours. Refluxing with stirring was continued for an additional hour. The reactants were cooled to about 85° C. Solids settled at a rate of about 15–20 inches per hour. The product was placed in a dry box and the supernatant liquid transferred to a bottle after less than one hour.

Analysis of the solution showed 2.4 weight percent magnesium, corresponding to a yield of 63 percent.

EXAMPLE 2

A one-liter straight-wall jacket reactor was equipped with a thermometer, mechanical stirrer, ice cooled condenser, and 250 ml addition funnel. The reactor was charged with 46.2 g (1.90 g-atom) of magnesium powder (Reade, −100 mesh), 4.25 g of powdered aluminum isopropoxide (Ventron), 540 ml of dry heptane and 30 ml of ethylisoamyl magnesium (From Ex. 1, 2.4 weight percent Mg). This was heated to 95° C. by means of the jacket through which was circulated kerosene. The addition funnel was charged with 100 ml heptane, 105 ml (0.865 mole) of isoamyl chloride (freshly distilled, Eastman), and 55.8 g (0.865 mole) of ethyl chloride (Ethyl). This mixture was added dropwise over 5 hours. A total of about 4.0 l of gas was evolved, VPC (Porapak Q, 100°) assay of which showed it to be about 50% ethyl chloride.

The mixture was stirred ½ hours longer at 95°–96° C., then cooled to 90° C. and allowed to settle.

The solution was decanted from the slurry layer giving a slightly cloudy solution. On standing the solution settled completely clear. It was decanted again and analyzed. Duplicate analyses showed 2.82; 2.83 weight percent Mg, for a yield of 75 percent based on the alkyl chlorides charged.

EXAMPLE 3

This example illustrates the attempted preparation of n-butyl-isobutylmagnesium.

Following the general procedure, 21.4 grams of magnesium, 375 ml of heptane, 20 ml of ethyl butyl magnesium (2.3 weight percent Mg) and 2.5 ml of diisobutylaluminum hydride were charged to the reactor and heated to 90° C. Afterwards 42 ml (0.40 mole) of n-butyl chloride was added, most of which was added dropwise over a period of one and one-half hours at a temperature of 95°–98° C. With about 5 ml remaining, 42 ml of isobutyl chloride was placed in the addition funnel and then added over a period of one and one half hours at a temperature of 94°–97° C. A yellow solid slowly formed along the wall where the iso-butyl chloride was dropped in. After addition was complete, the mixture was refluxed one hour longer, then cooled. The clear layer was decanted and analyzed. Magnesium content was found to be 0.24 weight percent.

EXAMPLE 4

This example illustrates the attempted preparation of isobutylethylmagnesium.

Using the apparatus and procedure hereinbefore, the flask was charged with 425 ml of heptane, 22.3 grams of magnesium powder, 20 ml of ethyl hexyl magnesium (2.2 weight percent Mg) and 1.9 ml of diisobutyl aluminum hydride. The mixture was heated to 92° C., and addition of 46 grams (0.498 mole) of 1-chloro-2-methyl propane and 21.4 grams (0.332 mole) of ethyl chloride was started. After about 15 minutes, a vigorous reaction occurred as was obvious by rapid refluxing. The reaction was controlled by using ice water to cool the reaction to 86°–87° C. Addition was continued while maintaining the reaction at reflux. All the alkyl chloride was added over about two hours after which time, the reflux temperature was down to 70° C. The magnesium compounds rapidly settled to give a clear solution. The magnesium had a faint yellow color. A sample of the clear solution was withdrawn and placed on filter paper. No solid remained after evaporation of the solvent. Addition of a few drops of isopropyl alcohol to 5 ml of the solution failed to give even a cloudy solution indicating no soluble magnesium compounds were formed.

EXAMPLE 5

This example illustrates the attempted preparation of diisobutylmagnesium. A mixture of 11.0 grams of magnesium powder, 200 ml of Isopar E, 15 ml of ethyl hexyl magnesium (2.72 weight percent Mg) and 1.3 ml of diisobutylaluminumhydride was heated in a reactor to 94° C. Heating was stopped and when the temperature began dropping 5.0 grams (0.036 mole) of hexyl chloride was added dropwise. Initiation was evident by a temperature rise to 97° C. Immediately, 35.2 grams (0.38 mole) of isobutyl chloride was placed in the addition funnel and addition began. A temperature of 98°–102° C. was maintained and addition was complete in one and three quarter hours. Stirring was continued an additional 45 minutes at 94°–95° C. The mixture was cooled to room temperature and transferred to the dry box. The clear solution was decanted. Analysis showed 0.62 weight percent magnesium.

From the foregoing examples it is clear that a new dialkylmagnesium compound, namely ethylisoamyl-magnesium has been produced in excellent yields contra to the teachings of the prior art.

In the terms "remotely branched chain alkyl magnesium" or "remotely branched chain alkyl chloride," "remotely branched chain alkyl" is defined as an alkyl group of at least five carbon atoms with branching occurring at least three carbon atoms from the magnesium group or the halide group, as the case may be.

Included in the foregoing are alkyl halides which are unbranched at the 1 and 2 postions relative to the halide group. Alkyl branches may occur at the 3 position and at postions further removed from the halide group.

The present invention has the utility of diorganomagnesium compounds as set forth hereinbefore, the additional utility of making such compounds and the further utility of solvating such compounds.

The composition of the invention is particularly useful as a catalyst component in the polymerization of olefins.

The foregoing disclosure and description of the invention is illustrative and explanatory thereof and various changes in the illustrated process may be made within the scope of the appended claims without departing from the spirit of the invention.

What is claimed is:

1. A hydrocarbon-soluble composition of matter comprising di-remotely branched chain alkyl magnesium and diethylmagnesium at a remotely branched chain alkyl: ethyl alkyl group ratio of from about 1:4 to about 4:1.

2. A composition according to claim 1, in which the remotely branched chain alkyl to ethyl alkyl group ratio is about 1:1 to 1:2.

3. A composition according to claim 1, including an organoaluminum viscosity reducing agent.

4. A composition according to claim 3, wherein said viscosity reducing agent is triethylaluminum.

5. A composition according to claim 3, wherein said viscosity reducing agent is diisobutylaluminum hydride.

6. A composition according to claim 3, wherein said viscosity reducing agent is aluminum isopropoxide.

7. A hydrocarbon-soluble composition of matter comprising diisoamylmagnesium and diethylmagnesium at an isoamyl:ethyl alkyl group ratio of from about 1:4 to about 4:1.

8. A composition according to claim 7, in which the isoamyl:ethyl alkyl group ratio is about 1:1 to 1:2.

9. A composition according to claim 7, including an organoaluminum viscosity reducing agent.

10. A composition according to claim 9, wherein said viscosity reducing agent is triethylaluminum.

11. A composition according to claim 9, wherein said viscosity reducing agent is diisobutylaluminum hydride.

12. A composition according to claim 9, wherein said viscosity reducing agent is aluminum isopropoxide.

13. A process for the manufacture of a hydrocarbon solution of a dialkylmagnesium comprising:
  (a) reacting, in the presence of a hydrocarbon solvent, magnesium metal with an ethyl halide and a remotely branched chain alkyl halide, to form a mixture of a hydrocarbon solution of a mixed dialkylmagnesium composition and undissolved solids; and,
  (b) separating the hydrocarbon solution from the undissolved solids.

14. The process of claim 13, wherein an organoaluminum viscosity reducing agent is added in step (a).

15. The process of claim 13, wherein all steps are conducted in a substantially moisture-free and oxygen free atmosphere.

16. The process of claim 13, wherein the ethyl halide is ethyl chloride.

17. The process of claim 13, wherein the hydrocarbon solvent is an aliphatic, cycloaliphatic, or aromatic hydrocarbon containing from 5 to 20 carbon atoms.

18. The process of claim 13, wherein the mole ratio of magnesium to total halides is about 1:0 to about 2.0.

19. A process for the manufacture of a hydrocarbon solution of a dialkylmagnesium composition comprising:
  (a) reacting, in the presence of a hydrocarbon solvent, magnesium metal with an ethyl halide and an isoamyl halide, to form a mixture of a hydrocarbon solution of a mixed dialkylmagnesium composition and undissolved solids; and,
  (b) separating the hydrocarbon solution from the undissolved solids.

20. The process of claim 19, wherein an organoaluminum viscosity reducing agent is added in step (a).

21. The process of claim 19, wherein all steps are conducted in a substantially moisture-free and oxygen-free atmosphere.

22. The process of claim 19, wherein the ethyl halide is ethyl chloride.

23. The process of claim 19, wherein the isoamyl halide is isoamyl chloride.

24. The process of claim 19, wherein the hydrocarbon solvent is a member selected from the group consisting of aliphatic, cycloaliphatic, and aromatic hydrocarbons containing from 5 to 20 carbon atoms.

25. The process of claim 19, wherein the mole ratio of magnesium to total halides is about 1.0 to about 2.0.

26. A composition of matter comprising:
  (a) diethylmagnesium
  (b) diisoamylmagnesium, and
  (c) a solvent selected from the group consisting of aliphatic, cycloaliphatic and aromatic hydrocarbons containing from about 5 to 20 carbon atoms.

27. A composition according to claim 26, wherein the concentration of the mixed dialkylmagnesium in the solvent is from about 0.2 weight percent to about 12 weight percent in terms of magnesium.

28. A composition according to claim 26, including (d) an organoaluminum viscosity reducing agent.

29. A composition according to claim 28, wherein the viscosity reducing agent is selected from the group consisting of trialkylaluminum, dialkylaluminum halide, alkylaluminum dihalide, dialkylaluminum hydride and aluminum alkoxide.

30. A composition according to claim 28, wherein the viscosity reducing agent is triethylaluminum, diisobutylaluminum hydride or aluminum isopropoxide.

* * * * *

UNITED STATES PATENT AND TRADEMARK OFFICE
CERTIFICATE OF CORRECTION

PATENT NO. : 4,396,554
DATED : August 2, 1983
INVENTOR(S) : GENE C. ROBINSON and BONNIE G. McKINNIE It is certified that error appears in the above-identified patent and that said Letters Patent is hereby corrected as shown below:

Column 2, line 48, reads "ca", should read --can--.

Column 4, line 39, reads "Example", should read --example--.

Column 4, line 64, reads "increased", should read --increases--.

Column 5, line 6, reads "halides other", should read --halides, other--.

Column 6, line 32, reads "consideration", should read --considerations--.

Column 10, line 16, reads "1:0 to about 2.0", should read --1.0 to about 2.0--.

Signed and Sealed this

Nineteenth Day of June 1984

[SEAL]

Attest:

Attesting Officer

GERALD J. MOSSINGHOFF

Commissioner of Patents and Trademarks